United States Patent [19]

Pinchuk

[11] Patent Number: 5,736,251
[45] Date of Patent: Apr. 7, 1998

[54] LUBRICIOUS SILICONE SURFACE MODIFICATION

[75] Inventor: Leonard Pinchuk, Miami, Fla.

[73] Assignee: Corvita Corporation, Miami, Fla.

[21] Appl. No.: 777,741

[22] Filed: Dec. 20, 1996

Related U.S. Application Data

[60] Continuation of Ser. No. 527,747, Sep. 13, 1995, abandoned, which is a division of Ser. No. 138,697, Oct. 18, 1993, abandoned.

[51] Int. Cl.⁶ ............................................... B32B 25/04
[52] U.S. Cl. .................... 428/447; 427/387; 428/425.5; 428/451; 428/391; 606/1; 623/1; 623/11
[58] Field of Search ........................ 427/387; 428/447, 428/391, 425.5, 451; 606/1; 623/1, 11

[56] References Cited

U.S. PATENT DOCUMENTS

| | | | |
|---|---|---|---|
| 3,240,731 | 3/1966 | Nitzsche et al. | 528/18 |
| 3,377,327 | 4/1968 | Gabriel | 260/853 |
| 3,460,975 | 8/1969 | Stebleton | 117/94 |
| 3,639,141 | 2/1972 | Dyck | 117/47 A |
| 3,708,324 | 1/1973 | Stebleton | 117/47 R |
| 3,844,989 | 10/1974 | Harumiya et al. | 260/17.4 R |
| 3,846,353 | 11/1974 | Grotta | 260/9 |
| 4,211,823 | 7/1980 | Suzuki et al. | 428/412 |
| 4,521,564 | 6/1985 | Solomon et al. | 525/54.1 |
| 4,539,232 | 9/1985 | Burzynski et al. | 427/387 |
| 4,820,302 | 4/1989 | Woodroof | 623/8 |
| 4,904,525 | 2/1990 | Taniguchi et al. | 428/328 |
| 5,053,048 | 10/1991 | Pinchuk | 623/1 |
| 5,069,965 | 12/1991 | Esemplare | 428/330 |
| 5,474,839 | 12/1995 | Ogawa et al. | 428/266 |

FOREIGN PATENT DOCUMENTS

| | | |
|---|---|---|
| 329041 | 8/1989 | European Pat. Off. |
| 497 204 A2 | 8/1992 | European Pat. Off. |
| 547550A1 | 6/1993 | European Pat. Off. |
| 3061533 | 3/1991 | Japan. |

OTHER PUBLICATIONS

Larm, Larsson and Olsson, "A New Non-Thrombogenic Surface Prepared by Selective Covalent Binding of Heparin Via a Modified Reducing Terminal Residue", Biomat., Med. Dev., Art. Org., 11(2&3), 161–173 (1983).

*Primary Examiner*—Margaret W. Glass
*Attorney, Agent, or Firm*—Lockwood, Alex, Fitzgibbon & Cummings

[57] ABSTRACT

Lubricious silicone surface modifying treatments and/or coatings for modifying the frictional or slip surface characteristics of shaped elastomeric articles are provided in surface modifications including a coating or surface modifying composition comprising:

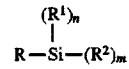

wherein R is selected from unsubstituted and halogen-substituted aliphatic, cycloaliphatic, aromatic and alkyl aromatic groups having less than or equal to about ten carbon atoms, $R^1$ is independently selected from hydrogen, hydroxyl, halogen, alkoxy and acyloxy groups, $R^2$ is independently selected from hydrogen, alkyl and halogen-substituted alkyl groups, n is an integer of 1 to 3 inclusive, and m=3−n. The cured, highly crosslinked, three dimensional silicone coatings are effective at reducing the coefficient of friction of surfaces of shaped elastomeric articles, such as those frequently used in medical devices, by a factors of from about 50% to about 80% as compared with the same uncoated substrates.

36 Claims, No Drawings

LUBRICIOUS SILICONE SURFACE MODIFICATION

This application is a continuation of application Ser. No. 08/527,747, filed Sept. 13, 1995, which is a division of application Ser. No. 08/138,697, filed Oct. 18, 1993, both of which are now abandoned

BACKGROUND OF THE INVENTION

The present invention generally relates to surface treatments and coatings intended to make the surfaces of objects more lubricious. More particularly, it relates to a new and improved highly crosslinked silane treatment effective to reduce the coefficient of friction of a surface by at least about 50% and as much as 80% or more compared to the coefficient of friction of the same untreated surface.

Natural and synthetic elastomers and polymers, especially silicone rubbers, are used for many medical applications because they are rather inert materials exhibiting good biocompatibility. Silicone rubbers and other natural and synthetic rubber materials suffer from poor surface lubricity, rendering their use in many medical and surgical applications undesirably problematic.

For example, pacemaker lead insulators made from silicone rubber do not easily slide past one another within the venous system, dramatically limiting their use in dual pacing applications. Hemostasis valves generally require the addition of silicone oils to enable catheters to slide through the valve opening. Many other medical devices such as penile implants suffer from poor lubricity when silicone tubes are inflated within silicone restraints. Poor contact surface lubricity causes sticking and/or hampered or unpredictable sliding performance, which may occur at inopportune times, such as during insertion of catheters. Poor slip characteristics between the catheter and the slide site may result in abrasion or erosion of the coating and stripped coating particles may contaminate the slide site. The surfaces of latex gloves are another example of a rubbery surface which must be powdered to facilitate or modify the surface friction properties to make it easier to slide the gloves on for use. The powder on the gloves gets everywhere and especially on surgical instruments which is undesirable.

Many prior chemistries and methods have been developed to render silicones and other rubbers more slippery, such as, for example, by the application of hydrophilic coatings, ion beam etching, and lubrication with silicone oils, to name but a few. Each of these prior methods suffers from unique problems.

More particularly, the coating of the silicone or other rubber surfaces with hydrophilic coatings, such as hydrogel coatings, poses a number of problems. First of all, the chemical bonding between the silicone or rubber surface and the hydrogel is frequently undesirably low, so that the hydrogel coating may be abraded, dislodged or removed from the surface of the rubber in its swollen state. The moisture content of the hydrogel must be carefully controlled because insufficient hydration results in stickiness. Even when fully hydrated, hydrogel-type coatings feel soapy when wet, which is often too slippery. A balance of properties is often very difficult to achieve with hydrogels because the resulting surfaces are either too slippery or they are sticky.

Hydrogel coatings, especially in the dry state, may also be ruptured and made to flake off in use. In many end use applications, catheters made of silicone rubber or other elastomeric materials are pulled, stretched, twisted, and bent which, because of differences in the elongation and flexural properties between the hydrogel coatings and the coated catheter, may cause the hydrogel coating to buckle, flake and fall off. Hydrogels also may not survive steam sterilization, which may cause excessive swelling and delamination to occur.

Although considerable effort has been expended in developing improved hydrophilic and hydrogel coatings, to date the above-mentioned disadvantages have yet to be satisfactorily solved.

Ion beam etching techniques are used to decrease the coefficient of friction of synthetic rubber surfaces. Etching methods suffer from an inherent inability or difficulty to be satisfactorily employed with surfaces having complicated geometries and surface configurations. Moreover, etched surfaces are relatively considerably more expensive to produce.

Silicone oil lubricants are also used to improve the lubricity of surfaces. Oil lubricants generally do not bond to the surface being treated. Generally, significant amounts of these oily surface lubricants must be used before the surface characteristics become truly slippery. The use of this type of slip modification agent on the surface of some medical devices may be impractical because leaching of silicone fluids into a body system, for example, may possibly occur, which depending on the context, may or may not be desirable.

In order to overcome the shortcomings of the prior art methods and coatings, it is an object of the present invention to provide a new and improved lubricious silicone surface treatment and/or coating for reducing the coefficient of friction of a surface of an elastomeric article.

It is another object of the present invention to provide a lubricious silicone coating for elastomeric articles which exhibits excellent lubricity and abrasion-resistance in use, even after gamma irradiation or steam sterilization.

It is a further object of the present invention to provide a new and improved lubricious coating capable of effectively reducing the coefficient of friction of a surface to less than 50% of its original, pre-treatment value.

It is still another object of the present invention to provide a highly cross-linked silane surface treatment capable of forming a lubricious texturized surface including a plurality of raised, hemi-spheroidal, micro-nodules, each having a lubricious cross-linked silane coating thereon.

It is still a further object of the present invention to provide a new and improved coating and coating method capable of satisfactorily providing long-lasting lubricity to complicated three dimensional surface configurations.

It is a another object of the present invention to provide shaped elastomeric silicone articles having an improved crosslink density.

It is still a further object of the present invention to provide a surface modification treatment and method for increasing the hardness of a silicone article and to improve its compression set and rebound resiliency properties.

SUMMARY OF THE INVENTION

In accordance with these and other objects, the present invention provides a new and improved curable lubricious surface modification for reducing the coefficient of friction of a surface of an elastomeric article, said surface modification including a surface modification composition comprising:

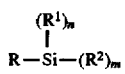

wherein R is selected from unsubstituted and halogen-substituted aliphatic, cycloaliphatic, aromatic and alkyl aromatic groups having less than or equal to about ten carbon atoms, $R^1$ is independently selected from hydrogen, hydroxy, halogen, alkoxy and acyloxy groups, $R^2$ is independently selected from hydrogen, alkyl and halogen-substituted alkyl groups, n is an integer of 1 to 3 inclusive, and m =3 −n. Optionally, the new and improved silane coating composition of this invention may include an organic solvent, preferably a non-polar organic solvent and optionally, may also include an organo-metallic or other crosslinking catalyst.

In accordance with the present invention, the new and improved silane surface modification and/or coating composition may be applied onto a surface to be treated by any suitable application means, including applying in the form of a solution or dispersion, for example, by spraying, dipping, brushing, rolling and the like or, without the need for solvents, by a vapor phase deposition method. The cross-linkable silane coating compositions may be cured upon standing at temperatures at or above room temperatures, for a time period sufficient to cure them, for example, a period of at least about 5 minutes or more. The new and improved coatings of this invention are cured or crosslinked preferably in the presence of moisture, including either atmospheric moisture or in artificially-controlled high humidity environments.

In accordance with an alternate aspect of the present invention, new and improved shaped elastomeric articles are provided in the form of two- or three-dimensionally shaped articles including a surface portion having a substantially reduced coefficient of friction. In accordance with this invention, the improved articles comprise: a shaped elastomeric article including a body portion and having at least one surface portion; and a firmly adherent, crosslinked surface modification or coating applied to the surface portion, said coating including a cross-linkable silane having the formula:

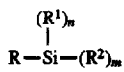

wherein R is selected from unsubstituted and halogen-substituted aliphatic, cycloaliphatic, aromatic and alkyl aromatic groups having less than or equal to about ten carbon atoms, $R^1$ is independently selected from hydrogen, hydroxy, halogen, alkoxy and acyloxy groups, $R^2$ is independently selected from hydrogen, alkyl and halogen-substituted alkyl groups, n is an integer of 1 to 3 inclusive, and m=3−n.

The shaped elastomeric articles which may be employed and treated in accordance with this invention to modify their surface friction characteristics may include naturally-occurring, as well as, synthetic elastomeric materials. Illustrative examples include: latex rubbers, soft polyurethanes, butyl rubber, butyl nitrile rubber, polyisoprenes, silicone rubbers, as well as various rubbery polymers and copolymeric materials. Each of these elastomeric surfaces and others generally may benefit from the treatment of this invention to reduce their surface tackiness, increase slipperiness and reduce their undesirably high coefficients of friction.

The shaped and surface treated or modified or coated articles may be put to various uses including generally any application in which a slippery or non-sticky surface characteristic is required. Medical applications are especially contemplated herein for various medical devices, such as pacer lead insulators, penile implant devices, breast implant devices, catheters, hemostasis valves, Foley balloon catheters, syringes and plungers, o-rings, gloves, condoms, shunts, stents and grafts. Other generally non-medical articles frequently made from natural or synthetic rubber, such as diving masks, boat hulls and the like, may also be used as the substrate to be coated or surface-modified.

Still another aspect of the present invention is to provide a method for reducing the coefficient of friction of a surface of an elastomeric article, said method comprising:

providing an elastomeric article having at least one surface portion to be treated;

contacting said surface portion with a curable coating composition including a cross-linkable silane having the formula:

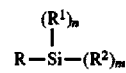

wherein R is selected from unsubstituted and halogen-substituted aliphatic, cycloaliphatic, aromatic and alkyl aromatic groups having less than or equal to about ten carbon atoms, $R^1$ is independently selected from hydrogen, hydroxy, halogen, alkoxy and acyloxy groups, $R^2$ is independently selected from hydrogen, alkyl and halogen-substituted alkyl groups, n is an integer of 1 to 3 inclusive, and m=3−n; and exposing the contacted surface portion to temperatures at or above room temperature in the presence of atmospheric moisture until formation of a firmly-adherent, cross-linked, lubricious, coefficient of friction-reducing coating on said surface portion is substantially complete.

Other objects and advantages of the present invention will become apparent from the following Detailed Description of the Invention and illustrative working Examples.

DETAILED DESCRIPTION OF THE INVENTION

In accordance with this invention, a lubricious silicone surface is provided on the surface of an article to improve the relative slipperiness of the surface and the non-tacky touch and feel and slidable performance of the article. The lubricious surface is provided in a coating which includes a surface modifying composition comprising:

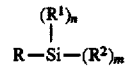

wherein R is selected from unsubstituted and halogen-substituted aliphatic, cycloaliphatic, aromatic and alkyl aromatic groups having less than or equal to about ten carbon atoms, $R^1$ is independently selected from hydrogen, hydroxy, halogen, alkoxy and acyloxy groups, $R^3$ is independently selected from hydrogen, alkyl and halogen-substituted alkyl groups, n is an integer of 1 to 3 inclusive, and m=3−n. Optionally, the new and improved silane coating composition of this invention may include an organic solvent, preferably a non-polar organic solvent and optionally, may also include an organo-metallic or other crosslinking catalyst.

It has been discovered that the silanes defined in the formula given above provide a densely cross-linked silicone coating or surface modification which is highly cross-linked and chemically bonded to the surface of the article being treated and which also forms a highly cross-linked three dimensional silicone matrix on the surface of the article, as well as a crosslinked interpenetrating network within the substrate. Cross-linking is presently believed to occur through the highly functionalized siloxane moieties or substituents on the silane which react in the presence of moisture to form silanol intermediates which in turn react directly with either: (a) OH moieties or OH-reactive groups present on the surface of the article or (b) which react directly with OH groups on neighboring silanes to build up the highly cross-linked, firmly-adherent three dimensional coating of this invention. In addition, it may be that higher processing and cure temperatures may break bonds within the substrate to expose or produce additional OH groups to further aid bonding. It has also been discovered that size of the R group constituent(s), i.e., the silane substituent(s), should be limited to groups containing about 10 carbon atoms or less to achieve good cross-linked density and good friction reducing properties. Employing silanes containing R groups which are too large, i.e., greater than 10 carbon atoms, has been observed to result in coatings which do not achieve or impart the desired degree of lubricity. Without wishing to be bound by any particular theory, it is believed that using silane moieties containing greater than 10 carbon atoms is less effective because the long chain silane R groups block portions of the surface to be coated during development of the coating matrix. This leaves surface areas on the surface of the article untreated so that the overall final surface obtained is less lubricious than that observed when using silanes containing the smaller R groups defined by the formula. The longer chain R groups may themselves be non-lubricious and accordingly they are less effective in reducing the relative stickiness of the elastomer surface.

In accordance with this invention, the preferred silanes will include those wherein the silane moiety or R group is selected from aliphatic, cycloaliphatic, aromatic and alkyl aromatic groups having less than or equal to 10 carbon atoms. The R groups may be unsubstituted or may be substituted with halogen groups such as chloro, bromo or fluoro groups or may be mixtures of any of the foregoing. Preferred silane moieties for use as the R group of the above formula are lower $C_1$–$C_8$ alkyl groups such as methyl, ethyl, propyl, and butyl and the like, as well as, halo-substituted alkyl, such as 1,1,1-trifluoropropyl, or an aromatic group, such as benzyl or tolyl groups.

In accordance with the formula, the preferred silanes for use in this invention will preferably include a maximum number of $R^1$ groups for maximum cross-link density and functionality. The $R^1$ groups may be any good silane leaving group which may be independently selected from hydrogen, halogen, hydroxyl, alkoxy, and acyloxy groups. Preferred groups for use as the $R^1$ substituent include methoxy, ethoxy, acetoxy, and the like, as well as mixtures thereof, or hydroxy or chloro groups. Especially preferred silanes are those in which n=3. In accordance with the above formula, when lower cross-linked functionality may be tolerated, the $R^2$ groups may be present which may be independently selected from hydrogen, alkyl and halogen substituted alkyl groups.

Specially preferred silanes within the scope of the above formula include methyltriacetoxysilane, ethyltriacetoxysilane, propyltriacetoxysilane, methyltrichlorosilane, ethyltrichlorosilane, and 1,1,1-trifluoropropyl-methyldimethoxysilane. The silanes in accordance with the formula are generally available commercially from several sources including Hüls America, Inc., Piscataway, N.J. Methods for making the silane monomers or coating precursors defined by the formula are generally well known to those skilled in this art.

Although trifunctional silanes are preferred, mixtures of any of the silanes defined by the formula might also be used, and mixtures of silanes of varying functionality might also be employed. In accordance with this invention, once the desired device and substrate surface are selected or treated or modified, if and as necessary, a three dimensional, highly cross-linked matrix containing silanes is formed on the surface. The silane is cured, cross-linked or polymerized in place on the surface to be rendered lubricious. This process is carried out in a manner such that a three dimensional matrix is formed. This matrix may be either a silane homopolymer or a copolymer derived from units defined in the above formula and reactive functional groups present on the substrate.

The silane homopolymer or copolymer forms a three dimensional matrix, which is a polymeric matrix different from that obtained or provided by a typical silane priming agent or coupling agent. Typical silane priming agents or coupling agents are applied in low concentration and with substantial quantities of a solvent, to provide what may be characterized as a silane monolayer, that is formed from solution. The three dimensional matrix according to the present invention is one in which the silane component is applied either without a solvent or with a diluent solvent.

In accordance with this invention, it is believed that the new and improved silane coating compositions cross-link chemically to the surface of the articles to be coated by reacting with OH groups present on the surface. The articles may comprise generally any polymeric, copolymeric, natural or synthetic elastomeric material including surface groups reactive with the silanes to form the three dimensional cross-linked coating matrix. Illustrative examples may include articles comprising polyamides, polyesters, polyurethanes, polysiloxanes, polyolefin polymers, rubbery copolymers, butyl rubbers, butyl nitrile rubbers, polyisoprenes, and the like. Although elastomeric substrates are primarily contemplated for use herein, these surface modifications and/or coatings might also improve the surfaces of metal or other materials if desired.

In accordance with this invention, the best results are achieved if the substrate surface is one in which the matrix formed in accordance with this invention is reactive in order to thereby provide especially advantageous adhesion and slip performance properties. Accordingly, preferred substrate materials are those which contain active hydrogen moieties. Exemplary substrate materials in this regard include acetoxy-derived silicones, silanol-terminated silicones, polyurethanes, nylons, and the like, each of which contain active hydrogen groups which are available to react directly with the silanes of the above formula to develop the coating matrix according to this invention.

In the event that it is desired to apply the lubricious coating to surfaces that are generally more inert than these types of preferred substrate materials, adhesion can be greatly facilitated by chemically treating such inert surfaces in order to provide hydroxyl groups on or near the surface thereof. Exemplary chemical surface treatments in this regard include such known procedures as chemical etching, surfactant adsorption, coextrusion, actinic radiation, such as plasma discharge, surface oxidation or reduction, and surface grafting with materials such as polyvinyl alcohol, poly(2-hydroxyethyl methacrylate) and the like. Bulk modifications of the substrate surface can also be accomplished in order to provide active hydrogens. Examples of conventional modifications of this type include blending with polymers having active hydrogens, partial degradation of polymers, end group modification, monomer functionalization, oxidation, reduction, copolymerization, and the like.

When a solvent diluent is used, the silane component will comprise at least about 2 percent by weight or more of the viscosity-adjusted composition. The solvents which may be employed may generally comprise any organic solvent in which the silanes of the formula are soluble or at least partially soluble at room temperatures. Illustrative examples include hydrocarbon solvents and halo-hydrocarbon solvents. Especially preferred solvents are non-polar and non-aromatic organic solvents. Illustrative solvents which may be used include: pentane, cyclohexane, heptane, xylene, short chain halohydrocarbons and silicone fluids, such as poly dimethylsiloxane oils, for example Dow Corning Medical Fluid 200 and the like. In other words, the composition that is used to form the three-dimensional matrix according to the present invention, if in the form of a solution, generally includes between about 2 weight percent and 100 weight percent of the silane component(s) used in forming the homopolymer or copolymer of the three dimensional matrix.

After the coating composition including the precursor components are applied onto the surface of the substrate, the reactive coating is cured as a thick film having a thickness of between about 0.01 and about 20 microns, with the thickness being substantially greater than that of silane priming agents or coupling agents that are applied in dilute solution to form monolayers, dilayers or trilayers, each having a thickness of less than ten Angstrom units. After application by any suitable means for forming a coating on the substrate surface, the silane containing coating is cured as a thick film, preferably in a humid oven, preferably before any rinsing, in order to minimize the chance that unreacted silane monomer would be removed prematurely with respect to curing and crosslinking to leave only a very thick primer layer.

Typically, the silane component may be dip coated onto the substrate to be rendered, although any other application means can be employed which allows for the easy application of a thick layer of the silane component. Once thus applied, the surface being rendered is subjected to drying conditions under controlled time, temperature and humidity conditions. Generally speaking, drying of the component so as to form the three-dimensional lubricious silicone coating matrix can be carried out for approximately twenty-four hours at room temperature, with it being possible to achieve the desired result in about ten minutes at a drying temperature of about 110° C. Variations in the time and temperature protocols employed to effect curing may be used. A typically preferred time and temperature combination is to carry out the drying for about two hours at approximately 80° C. Generally, the item to be coated is immersed in a coating solution for a period of about 2 to about 10 minutes and is then removed from the solution and immediately placed in an oven for curing. The temperature and time of cure are dependent upon the type or types of silane used. For example, ethyltriacetoxysilane requires a temperature in excess of 60° C. and cure time of at least about 1 hour to cure satisfactorily. A preferred time and temperature for curing this silane is 60 minutes at 150° C. Ethyltrichlorosilane may be cured at room temperature over a time period of about one to two hours.

Another method to coat devices is by vapor deposition where the silane is heated and the device is placed in its vapors. Vacuum may or may not be used during the deposition process. Still another method for coating devices is by spray coating where the silane, or silane and solvent and/or catalyst is sprayed out of a container, such as an air brush device, and is coated onto the surface of the substrate device.

With respect to the humidity conditions in effect during the curing or three-dimensional matrix formation procedure, it is preferred that the humidity be controlled in order to thereby enhance the formation of the three-dimensional matrix. It is preferred to control the humidity conditions such that a higher relative humidity environment is provided at the early stages of the curing or drying operation, with a decrease in the relative humidity near the end of the curing procedure. For example, at the beginning of the curing procedure, a 50 percent to 70 percent relative humidity environment will enable hydrolysis of the silane component in the earlier stages of the curing procedure, while the humidity can be decreased to a relative humidity of 20 percent or below in order to thereby facilitate evaporation of any residual water or moisture toward the end of the curing step in order to thereby complete the formation of a three-dimensional matrix.

In general, the surface portion of the device being treated can be exposed to temperatures at or above room temperature. For example, the contacted surface portion can be exposed to elevated temperatures of greater than or equal to 50° C. for a period of equal to or greater than about 5 minutes.

After this silanation reaction during which the silane homopolymer or copolymer is formed has been completed, the formed three-dimensional silane matrix is able to be rinsed repeatedly in water or organic solvents without substantially modifying the three-dimensional matrix which is provided. Rinsing of the matrix is preferably carried out repeatedly after curing is complete in order to remove any as yet unreacted or unbound silane or polymer residue within the matrix.

It has been observed that curing of coatings of this invention on pre-humidified substrates and/or in high relative humidity controlled environments may cause the coated surfaces to take on the appearance of very small droplets which also penetrate and bond into the surface. These bumpy, lumpy, hemi-spheroidal, micro-nodular coating matrix formations are desirable because they are believed to result in the greatest reduction in the surface coefficients of friction for the coated articles. The lumpy nodularized surfaces may improve the lubricity by preventing surface to surface contact by a spacer action of the lumps. Curing reactions performed in less humid environments and/or without pre-humidification or moisturization of the substrate to be modified or coated still provide very useful lubricious coatings which effectively reduce surface friction characteristics and tackiness. It has been simply observed that the texturized or micro-nodularized silicone coatings provide a greater reduction in the surface coefficient of friction and for this reason coatings and coated articles having this kind of surface modification are especially preferred.

In accordance with this invention, the coating compositions may optionally include a minor effective amount of a cross-linking catalyst which is effective to promote more complete or more rapid curing of the coatings at a given desired cure temperature range. Generally, known siloxane catalysts familiar to those skilled in this art may be used including organo-metallic catalysts based on lead, tin, zinc and titanium compounds, as well as, quaternary compound catalysts. The catalysts may be used in amounts ranging from 0.0001% to about 1.0% by weight, based upon the total weight of silane component(s). Especially preferred catalysts include dialkylmetal mono-or polycarboxylates, such as stannous octoate, dibutyltin dilaurate and dibutyltin diacetate.

Optionally, lubricants may be added to the coatings of this invention if desired. In this connection it has been observed that if lubricants such as silicone lubricants like silicone oils are applied to the coated surfaces of this invention, good slip performance and lubrication are achieved using significantly smaller quantities of the silicone oil lubricant than are required to be used to achieve the same surface slipperiness on articles not coated with the coatings of this invention. The ability to achieve the same lubrication levels using less added silicone oil means that less oil can be used and that there is a decreased possibility for excess lubricating oil lubricant to leach away from the substrate surface in use.

Other advantages provided by the present invention will become apparent from the following illustrative Examples.

DESCRIPTION OF THE PREFERRED EMBODIMENTS

EXAMPLE 1

A curable lubricious silicone coating composition in accordance with this invention was prepared, coated on a medical device substrate, cured and tested for relative stickiness, tackiness and surface coefficient of friction properties. The coating composition was prepared by mixing the following ingredients in a 9×9 inch stainless steel pan until dissolution was complete:

| Component | Weight, in grams |
| --- | --- |
| Methyltriacetoxysilane | 1.0 |
| Ethyltriacetoxysilane | 1.0 |
| Dibutyltin diacetate | 0.03 |
| Heptane | 40.00. |

A surface modified elastomeric shaped article was prepared in accordance with invention as follows:

A silicone hemostasis valve was immersed in the solution prepared above for ten minutes and then removed and placed in an oven at 110° C. for ten minutes. The coated valve was removed from the oven and permitted to cool, it was rinsed several times with deionized (DI) water and it was noted that a firmly adherent, cross-linked coating was present on the valve surface and penetrated within the bulk of the device.

The coefficient of friction of the surface of the coated hemostasis valve and an untreated hemostasis valve were compared by applying a load on a clamped specimen parallel to the surface at a constant rate and measuring the force required to overcome the surface friction using a modified Instron® test device.

The coefficient of friction of the hemostasis valve coated with the lubricious silicone prepared in accordance with Example 1 had a surface coefficient of friction which was five times less than that measured for the untreated control, i.e., surface friction was reduced by 80%.

EXAMPLE 2

A number of test specimens were prepared and tested for relative lubricity by taking ¼inch diameter silicone tubing cut into six-inch lengths. Some of the test specimens were surface modified by soaking in a 5% solution of ethyltriacetoxysilane in heptane for a period of 10 minutes. Thereafter, the soaked specimens were cured by heating in a drying oven set a 150° C. for a period of one hour. The surface modified test specimens were then rinsed with DI water three times and permitted to air dry.

The modified test specimens were compared to other untreated test specimens for differences in surface friction characteristics in accordance with a modified test procedure. In accordance with the test method, the tubing specimens were clamped in a fixed jaw of an Instron machine so that opposing sidewalls of the tubing were in contact with each other. An adjacent free end portion of the tubing was clamped in a movable jaw located adjacent the fixed jaw at the start of the test. The movable jaw was moved laterally to pull the tubing lengthwise through the fixed jaw at a constant rate and the pounds force required to slip the tubing through the fixed jaws was noted. In accordance with this experimental procedure, higher force values indicate lower surface lubricity. The load range was set at about 10 pounds and the speed was set at 5 inches per minute. Six untreated tubing specimens were compared with six treated specimens prepared above in accordance with this invention. The results obtained were as follows:

| Test Speciment | Slip Force, in Lbs. |
| --- | --- |
| Untreated | 4.5, 7.4, 4.7, |
|  | 5.4, 3.8, and 7.4 (mean = 5.53) |
| Treated | 0.9, 1.2, 1.5, |
|  | 1.5, 1.1, and 1.3 (mean = 1.25) |

The above test demonstrated that the surface modification treatment of this invention reduced surface friction characteristics and improved surface lubricity by greater than 75% over the untreated control specimens.

EXAMPLE 3

A solution was made of 5% ethyltriacetoxy silane in 1,1,1-trichloroethane. A silicone rubber catheter was immersed in this solution for 5 minutes then placed in an oven at 150° C. for one hour. The resulting catheter surface was rendered lubricious and easily passed through a polyethylene introducer.

EXAMPLE 4

Ethyltriacetoxysilane (50 ml) was poured into a 400 ml beaker and heated on a hot plate until a vapor evolved from the surface of the beaker (about 100° C.). The thin balloon section of a silicone rubber Foley catheter was rotated in the evolving fumes for two minutes then placed in an oven at 150° C. to cure for one hour. The cured balloon catheter was no longer sticky and readily passed through a hemostasis valve.

EXAMPLE 5

A solution of 5% propyltrichlorosilane in cyclohexane was placed in the reservoir of an air brush and sprayed onto a natural rubber latex glove. The treated glove was dried overnight at room temperature. The treated glove was not sticky as compared to an untreated control glove which required powder to render it non-sticky.

EXAMPLE 6

A small amount of ethyltrichlorosilane was poured into an Erlenmeyer flask and a butyl nitrile syringe plunger fixtured above the liquid. A vacuum was pulled into the flask for 2 minutes and then released and the sample removed and cured in an oven at 110° C, for 10 minutes. The plunger was more lubricious than untreated controls and did not require a silicone lubricant in the assembled syringe.

EXAMPLE 7

A urethral valve catheter equipped with a silicone balloon portion was pre-humidified and vapor-phase treated with methyltriacetoxysilane as set forth in the method of Example 4. After curing for one hour at 150° C., the catheter was cooled. The balloon portion was expanded and examined for surface tackiness by touch. The surface treated portion had a micro-nodularized surface treated portion that felt smooth and slippery to the touch. When the balloon portion was cut open, micro nodules of silane surface treatment were observed on the interior surface of the balloon which was not directly contacted with the silane vapors. From this observation, it was concluded that the silane treatment of this invention penetrated the bulk of the balloon catheter substrate and was not only a surface coating.

EXAMPLE 8

The ability of the surface modification treatment of this invention to increase the cross-link density of silicone substrates, as measured by an increase in Durometer hardness was determined. In accordance with this test, a sample of silicone tubing was surface treated in accordance with the method of Example 3. The treated tubes were evaluated against untreated control specimens in a standard test for Durometer hardness. The treated specimens showed an increased value of 70A hardness as compared with the 60A values measured on the untreated specimens.

Hemostasis valves were also evaluated to determine if the surface modification treatment of this invention was effective to increase their durometer hardness over untreated hemostasis valve controls. The test results showed an increase in hardness of from shore 40A to 47A for the treated hemostasis valves over the untreated controls.

From these experiments and from physical manipulation of various treated substrates, it has been concluded that silicone rubber substrates treated with the silane surface modifications of this invention exhibited better hardness, better compression set, better rebound resilience and better hysteresis properties over untreated substrates.

Although the present invention has been described with as reference to certain preferred embodiments, modifications or changes may be made by those skilled in the art. For example, instead of a one time surface treatment, desired substrates may repeatedly be contacted with the silane treatment and cured to provide a laid up surface treatment. All such obvious changes may be made by those skilled in this art, without departing from the scope and spirit of the present invention and defined in the appended claims.

What is claimed is:

1. A lubricious surface coating for reducing the coefficient of friction of a surface of an elastomeric article, said surface coating including a surface modifying composition consisting essentially of a crosslinked silane which, prior to crosslinking, had the formula:

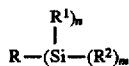

wherein R is a moiety selected from the group consisting of unsubstituted and halogen-substituted aliphatic, cycloaliphatic, aromatic and alkyl aromatic groups having less than or equal to about ten carbon atoms, $R^1$ is a moiety independently selected from the group consisting of hydrogen, hydroxy, halogen, alkoxy and acyloxy groups, $R^2$ is a moiety independently selected from the group consisting of hydrogen, alkyl and halogen-substituted alkyl groups, n is an integer of 1 to 3 inclusive, and m=3-n; and said crosslinked silane is a firmly adherent matrix crosslinked with the surface of the elastomeric article, which matrix has a thickness of between about 0.01 and about 20 microns and forms a plurality of raised micro-nodules which penetrate and bond into the surface of the elastomeric article and which reduce the coefficient of friction of the surface of the elastomeric article.

2. A lubricious coating as defined in claim 1, wherein in the formula R is $C_1$–$C_8$ alkyl, $R^1$ is acetoxy and n=3.

3. A lubricious coating as defined in claim 1, wherein in the formula R is $C_1$–$C_8$ alkyl inclusive, $R^1$ is chloro and n=3.

4. A lubricious coating as defined in claim 1, wherein in the formula R is polyhalogen-substituted alkyl having from about 1 to about 8 carbon atoms inclusive, $R^1$ is methoxy, $R^2$ is methyl, n=2 and m=1.

5. A lubricious coating as defined in claim 1, wherein the silane is methyltriacetoxysilane.

6. A lubricious coating as defined in claim 1, wherein said silane is ethyltriacetoxysilane.

7. A lubricious coating as defined in claim 1, wherein said silane is propyltriacetoxysilane.

8. A lubricious coating as defined in claim 1, wherein said silane is ethyltrichlorosilane.

9. A lubricious coating as defined in claim 1, wherein said silane is 1,1,1-trifluoropropyl-methyldimethoxysilane.

10. A lubricious coating as defined in claim 1, further comprising an organic solvent.

11. A lubricious coating as defined in claim 10, wherein said solvent comprises a non-polar organic solvent.

12. A lubricious coating as defined in claim 1, further comprising a minor effective amount of a crosslinking catalyst for promoting crosslinking and curing reactions between the silanes and between the silanes and a surface being coated.

13. A curable lubricious coating as defined in claim 12, wherein said catalyst is selected from the group consisting of organometallic catalysts based on lead, tin, zinc and titanium compounds.

14. A curable lubricious coating as defined in claim 13, wherein said catalyst is selected from the group consisting of stannous octoate and dibutyltin dilaurate.

15. A lubricious coating as defined in claim 10, further comprising a minor effective amount of a crosslinking catalyst for promoting crosslinking and curing reactions between the silanes and between the silanes and a surface being coated.

16. A lubricious coating as defined in claim 1, further including a lubricant.

17. A lubricious coating as defined in claim 16, wherein said lubricant is a silicone lubricant.

18. A lubricious coating as defined in claim 17, wherein said silicone lubricant is a silicone oil.

19. A shaped elastomeric article including at least one surface portion characterized by having a reduced coefficient of friction, said article comprising:

a shaped elastomeric article including a body having at least one elastomeric surface portion; and a firmly-adherent matrix coating crosslinked with said surface portion, said matrix coating having a thickness of between about 0.01 and about 20 microns and consisting essentially of crosslinked silane micro-nodules which are raised above and which penetrate and bond into the elastomeric surface portion, which raised micro-nodules reduce the coefficient of friction of the elastomeric surface portion, said crosslinked silane, prior to cross-linking, had the formula:

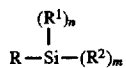

wherein R is a moiety selected from the group consisting of unsubstituted and halogen-substituted aliphatic, cycloaliphatic, aromatic and alkyl aromatic groups having less than or equal to about ten carbon atoms, $R^1$ is a moiety independently selected from the group consisting of hydrogen, hydroxy, halogen, alkoxy and acyloxy groups, $R^2$ is a moiety independently selected from the group consisting of hydrogen, alkyl and halogen-substituted alkyl groups, n is an integer of 1 to 3 inclusive, and m=3−n.

20. A shaped article as defined in claim 19, wherein the coated surface portion has a coefficient of friction of less than about 50% of the value for the coefficient of friction of an uncoated, untreated surface of said body.

21. A shaped article as defined in claim 19, wherein said shaped elastomeric article comprises a non-synthetic or a synthetic elastomeric material.

22. A shaped article as defined in claim 21, wherein said elastomeric material is a molded, extruded or dip-coated thermoplastic material.

23. A shaped article as defined in claim 22, wherein said thermoplastic material is selected from the group consisting of polyolefins, vinyl-addition polymers, polyamides, polyesters, polyurethanes, and polysiloxanes.

24. A shaped article as defined in claim 19, further comprising a thin lubricating layer of a silicone oil disposed on said silane coated surface.

25. A shaped article as defined in claim 19, wherein said shaped article is a medical device selected from tubing, catheters, gloves, condoms, prostheses, implants, valves, insulated leads, scopes, syringes, o-rings, stents, shunts, grafts, or infusion equipment.

26. A shaped article as defined in claim 19, wherein said shaped article is a rubbery shaped article adapted to make contact with the human body.

27. A shaped article as defined in claim 19, wherein said shaped article is adapted for use in marine or aquatic environments.

28. A shaped article as defined in claim 19, wherein R is $C_1$–$C_{10}$ alkyl.

29. A method for reducing the coefficient of friction of a surface of an elastomeric article, said method comprising:
providing an elastomeric article having at least one surface portion to be treated;
contacting said surface portion with a curable surface modifying composition consisting essentially of a crosslinkable Silane having the formula:

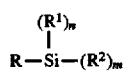

wherein R is a moiety selected from the group consisting of unsubstituted and halogen-substituted aliphatic, cycloaliphatic, aromatic and alkyl aromatic groups having less than or equal to about ten carbon atoms, $R^1$ is a moiety independently selected from the group consisting of hydrogen, hydroxy, halogen, alkoxy and acyloxy groups, $R^2$ is a moiety independently selected from the group consisting of hydrogen, alkyl and halogen-substituted alkyl groups, n is an integer of 1 to 3 inclusive, and m=3−n ; and exposing the contacted surface portion to temperatures at or above room temperature in the presence of moisture in order to form a firmly-adherent, lubricious, coefficient of friction-reducing surface modification on said surface portion, said surface modification having a thickness of between about 0.01 and about 20 microns and being a matrix of a plurality of micro-nodules which are raised above said surface portion in order to reduce the coefficient of friction of said surface portion.

30. A method as defined in claim 29, further comprising the step of pre-humidifying the surface to be treated before said contacting step.

31. A method as defined in claim 29, wherein said contacting step is performed by vapor phase deposition.

32. A method as defined in claim 29, wherein said contacting step is performed by applying a solution of said silane onto said surface portion.

33. A method as defined in claim 32, wherein said contacting step is performed by immersing the surface portion into said silane solution.

34. A method as defined in claim 29, wherein in said exposing step, the contacted surface portion is exposed to elevated temperatures of greater than or equal to 50° C. for a period of greater than or equal to about 5 minutes.

35. A method as defined in claim 29, further comprising, after said exposing step, applying a lubricant to said coated surface portion.

36. A method for increasing the crosslink density, relative hardness and rebound resiliency of an elastomeric article, said method comprising:
providing an elastomeric article to be treated having at least one surface portion;
contacting said surface portion with a curable surface modifying composition consisting essentially of a crosslinkable silane having the formula:

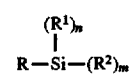

wherein R is a moiety selected from the group consisting of unsubstituted and halogen-substituted aliphatic, cycloaliphatic, aromatic and alkyl aromatic groups having less than or equal to about ten carbon atoms, $R^1$ is a moiety independently selected from the group consisting of hydrogen, hydroxy, halogen, alkoxy and acyloxy groups, $R^2$ is a moiety independently selected from the group consisting of hydrogen, alkyl and halogen-substituted alkyl groups, n is an integer of 1 to 3 inclusive, and m=3−n ; and exposing the contacted surface portion to temperatures at or above room temperature in the presence of moisture in order to form a firmly-adherent, lubricious, coefficient of friction-reducing surface modification on said surface portion, said surface modification having a thickness of between about 0.01 and about 20 microns and being a matrix of a plurality of micro-nodules which are raised above said surface portion in order to reduce the coefficient of friction of said surface portion.

* * * * *

UNITED STATES PATENT AND TRADEMARK OFFICE
CERTIFICATE OF CORRECTION

PATENT NO. : 5,736,251
DATED : April 7, 1998
INVENTOR(S) : Leonard Pinchuk

Page 1 of 2

It is certified that error appears in the above-identified patent and that said Letters Patent is hereby corrected as shown below:

On the Title Page, in the Abstract, lines 16-17, "by a factors of" should read --by a factor of--.
Col. 1, line 7, insert a period --.-- after "abandoned".
Col. 2, line 52, "It is a another" should read --It is another--.
Col. 3, line 12, "m =3 -n" should appear as --m=3-n--.
Col. 4, after line 50, indent line 51 and insert --a cross-linkable silane having the formula:--; line 60, delete "$R^3$" and insert --$R^2$--.
Col. 5, line 67, delete the hyphen between "trifluoropropyl" and "methyldimethoxysilane".
Col. 9, line 39, in the table, "40.00." should read --40.00--; line 42, "with invention" should read --with the invention--; line 65, "½inch" should read --½ inch--.
Col. 10, line 3, "oven set a" should read --oven set at--; line 26, in the table heading, "Test Speciment" should read --Test Specimen--.

UNITED STATES PATENT AND TRADEMARK OFFICE
CERTIFICATE OF CORRECTION

PATENT NO.  : 5,736,251
DATED       : April 7, 1998
INVENTOR(S) : Leonard Pinchuk It is certified that error appears in the above-identified patent and that said Letters Patent is hereby corrected as shown below:

Col. 11, line 38, "shore 40A to 47A" should read --shore 40A to shore 47A--; lines 46-47, "with as reference" should read --with reference--; lines 61-65, claim 1, replace the formula with --

$$R-(Si)-(R^2)_m \text{ with } (R^1)_n \text{ attached}$$

--.

Col. 12, line 43, claim 13, delete "curable"; line 47, claim 14, delete "curable".

Col. 13, line 58, delete "Silane" and insert --silane--.

Signed and Sealed this

Twenty-sixth Day of October, 1999

Attest:

Q. TODD DICKINSON

*Attesting Officer*     *Acting Commissioner of Patents and Trademarks*